US00PP25646P2

(12) United States Plant Patent
Lemonnier

(10) Patent No.: US PP25,646 P2
(45) Date of Patent: Jun. 23, 2015

(54) ***HELLEBORUS* PLANT NAMED 'LEM 100'**

(50) Latin Name: *Helleborus niger×(Helleborus×hybridus)*
Varietal Denomination: LEM 100

(71) Applicant: Martine Lemonnier, Beaumont le Hareng (FR)

(72) Inventor: Martine Lemonnier, Beaumont le Hareng (FR)

( * ) Notice: Subject to any disclaimer, the term of this patent is extended or adjusted under 35 U.S.C. 154(b) by 155 days.

(21) Appl. No.: 13/986,830

(22) Filed: Jun. 10, 2013

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'LEM 100', characterized by its compact, upright and mounding plant habit; freely flowering habit; single red purple-colored flowers; and good garden performance.

2 Drawing Sheets

Botanical designation: *Helleborus niger*×(*Helleborus*×*hybridus*).

Cultivar denomination: 'LEM 100'.

BACKGROUND OF THE INVENTION

The present invention relates to a new and distinct cultivar of *Helleborus* plant, botanically known as *Helleborus niger*×(*Helleborus*×*hybridus*) and hereinafter referred to by the name 'LEM 100'.

The new *Helleborus* plant is a product of a planned breeding program in Beaumont le Hareng, France. The objective of the breeding program was to create new uniform *Helleborus* plants with unique leaf and flower coloration and pest resistance.

The new *Helleborus* plant originated from a cross-pollination conducted by the Inventor in Beaumont le Hareng, France in February, 1993 of an unnamed proprietary seedling selection of *Helleborus niger*, not patented, as the female, or seed, parent with an unnamed proprietary seedling selection of *Helleborus*×*hybridus*, not patented, as the male, or pollen, parent. The new *Helleborus* plant was discovered and selected by the Inventor as a single flowering plant from within the progeny of the stated cross-pollination grown in a controlled greenhouse environment in Beaumont le Hareng, France in February, 1995.

Asexual reproduction of the new *Helleborus* plant by divisions in a controlled greenhouse environment in Beaumont le Hareng, France since February, 1996 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'LEM 100'.

These characteristics in combination distinguish 'LEM 100' as a new and distinct *Helleborus* plant:

1. Compact, upright and mounding plant habit.
2. Freely flowering habit.
3. Single red purple-colored flowers.
4. Good garden performance.

Compared to plants of the parent selections, plants of the new *Helleborus* are more uniformly mounded and are more freely flowering.

Plants of the new *Helleborus* can be compared to plants of *Helleborus niger*×*Helleborus lividus* 'COSEH 710', disclosed in U.S. Plant Pat. No. 21,063. In side-by-side comparisons conducted in Beaumont le Hareng, France, plants of the new *Helleborus* differed from plants of 'COSEH 710' in the following characteristics:

1. Plants of the new *Helleborus* were more compact than and not as vigorous as plants of 'COSEH 710'.
2. Plants of the new *Helleborus* started flowering in January whereas plants of 'COSEH 710' started flowering in December.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'LEM 100' grown in a container.

The photograph on the second sheet is a close-up view of a typical flowering plant of 'LEM 100'.

DETAILED BOTANICAL DESCRIPTION

The aforementioned photographs and following observations, measurements and values describe plants grown during the winter in two-liter containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus hybridus* 'LEM 100'.

Parentage:

*Female, or seed, parent*.—Unnamed proprietary seedling selection of *Helleborus niger*, not patented.

*Male, or pollen, parent*.—Unnamed proprietary seedling selection of *Helleborus×hybridus*, not patented.

Propagation:

*Type*.—By tissue culture.

*Time to initiate roots, winter*.—About two months at 12° C.

*Time to produce a rooted young plant, winter*.—About six months at 4° C. to 15° C.

*Root description*.—Thick to thin, fleshy; white to brown in color.

*Rooting habit*.—Sparse.

Plant description:

*Plant and growth habit*.—Herbaceous perennial; compact, upright and mounding plant habit with flowers held above the foliar plane; plant shape is flattened globular; low to moderately vigorous growth habit.

*Plant height*.—About 18.7 cm.

*Plant diameter* (*area of spread*).—About 39.3 cm.

Leaf description:

*Arrangement*.—Leaves arranged alternately in a basal rosette; leaves palmately compound with about five leaflets per leaf.

*Leaf length*.—About 16.3 cm.

*Leaf width*.—About 19.3 cm.

*Leaflet length*.—About 9.9 cm.

*Leaflet width*.—About 5.3 cm.

*Leaf shape*.—Palmate; orbicular to reniform in outline.

*Leaflet shape*.—Obovate.

*Leaflet apex*.—Acute.

*Leaflet base*.—Attenuate.

*Leaflet margin*.—Distally, serrate; proximally, entire.

*Leaflet texture, upper and lower surfaces*.—Smooth, glabrous; leathery.

*Leaflet venation pattern*.—Pinnate.

*Leaflet color*.—Developing leaves, upper and lower surfaces: Close to 144A. Fully developed leaves, upper surface: Between 147A and N189A; venation, close to 144A to 144B. Fully developed leaves, lower surface: Close to 147B; venation, close to 187A to 187B. Petioles: Length: About 11.8 cm. Diameter: About 7 mm. Texture, upper and lower surfaces: Smooth, glabrous. Color, upper and lower surfaces: Close to 143C; towards the base, densely dotted with close to 187B to 187C.

Flower description:

*Flower shape and habit*.—Single-type rotate flowers arranged in terminal and axillary panicles; freely flowering habit with typically about two to three open flowers per panicle and about 16 flowers developing per plant; flowers face outwardly to drooping.

*Fragrance*.—None detected.

*Natural flowering season*.—Plants begin flowering about ten months after planting; plants flower from winter to early spring in Germany.

*Flower longevity on the plant*.—About ten days; flowers persistent.

*Inflorescence height*.—About 9.8 cm.

*Inflorescence diameter*.—About 9 cm.

*Flower buds*.—Length: About 2.4 cm. Diameter: About 1.2 cm. Shape: Ovate. Color: Close to 157A heavily tinged with close to 184C to 184D.

*Flower diameter*.—About 7.4 cm.

*Flower depth* (*height*).—About 2.7 cm.

*Petals*.—Transformed into nectaries. Quantity: About eleven. Length: About 1 cm. Width: About 4 mm. Shape: Flattened tubular. Texture, upper and lower surfaces: Smooth, glabrous; slightly glossy. Color: When opening, upper and lower surfaces: Close to 143C and 144B; towards the apex, close to 145B to 145C. Fully opened, upper and lower surfaces: Close to 152B; towards the apex, close to 154B.

*Sepals*.—Quantity and arrangement: Five arranged in a single whorl. Length: About 4.2 cm. Width: About 4 cm. Shape: Broadly ovate to nearly orbicular. Apex: Obtuse to rounded. Base: Broadly cuneate. Margin: Entire. Texture, upper and lower surfaces: Smooth, glabrous. Color: When opening, upper surface: Close to NN155B heavily tinged with close to 71B. When opening, lower surface: Close to 69B heavily tinged with close to 70B. Fully opened, upper and lower surfaces: Close to 70B; color becoming closer to 186A to 186B with development.

*Peduncles*.—Length: About 19.5 cm. Diameter: About 7 mm. Strength: Moderately strong. Aspect: About 25° from vertical. Texture: Smooth, glabrous. Color: Close to 146D heavily dotted with close to 187C to 187D especially towards the base.

*Pedicels*.—Length: About 4.3 cm. Diameter: About 3 mm. Aspect: About 30° from peduncle axis. Strength: Moderately strong. Texture: Smooth, glabrous. Color: Close to 146D heavily dotted with close to 187C to 187D especially towards the base.

*Reproductive organs*.—Stamens: Quantity per flower: About 100. Filament length: About 1.6 cm. Filament color: Close to NN155D. Anther shape: Reniform. Anther length: About 2 mm. Anther color: Close to 154C to 154D. Pollen amount: Moderate. Pollen color: Close to 5D. Pistils: Quantity per flower: About five. Pistil length: About 1.2 cm. Stigma shape: Club-shaped. Stigma color: Close to 155A. Style length: About 1.1 cm. Style color: Close to 186A. Ovary color: Close to 150C.

*Seeds and fruits*.—Seed and fruit development have not been observed on plants of the new *Helleborus*.

Garden performance: Plants of the new *Helleborus* have been observed to have good garden performance and to tolerate rain, wind, high temperatures of about 35° C. and are hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'LEM 100' as illustrated and described.

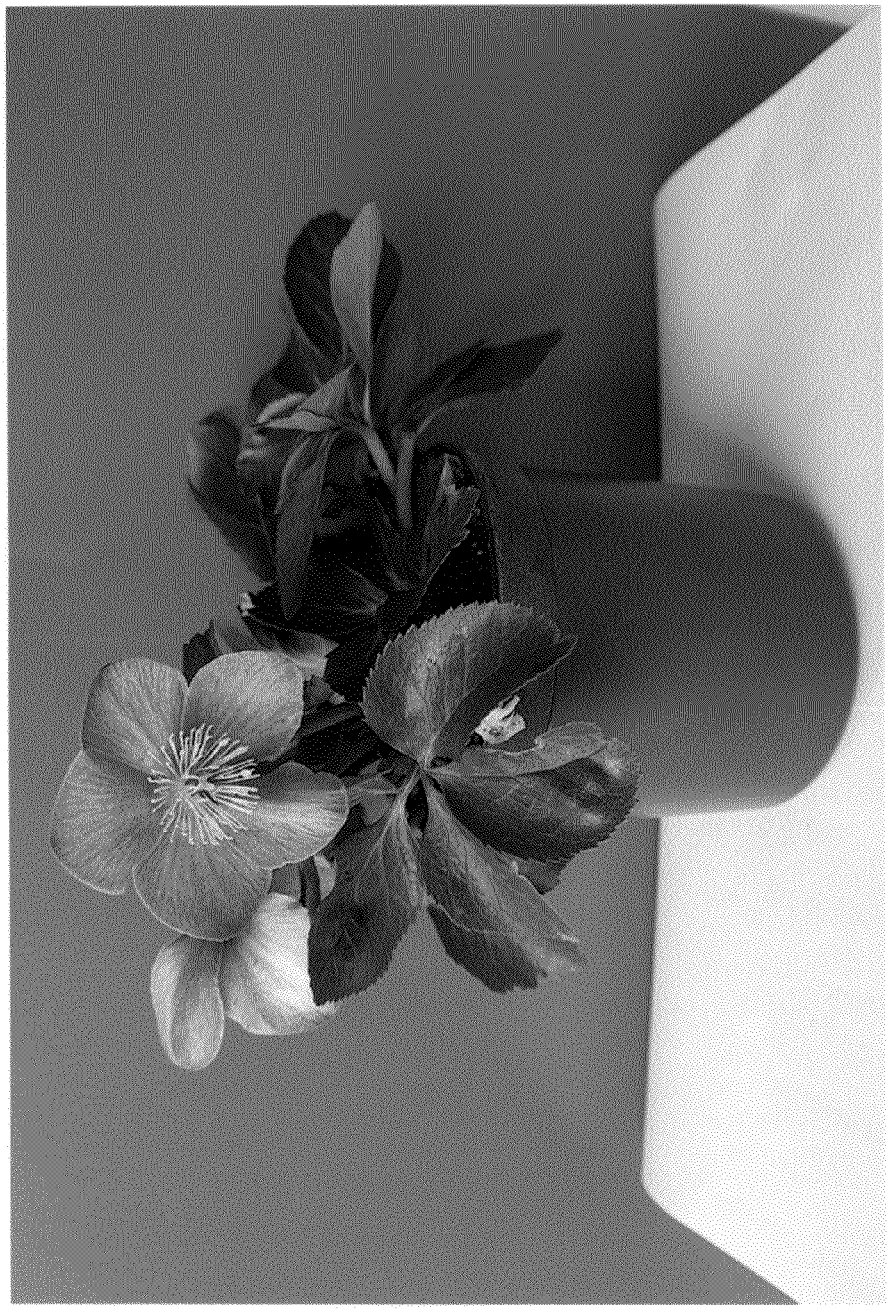

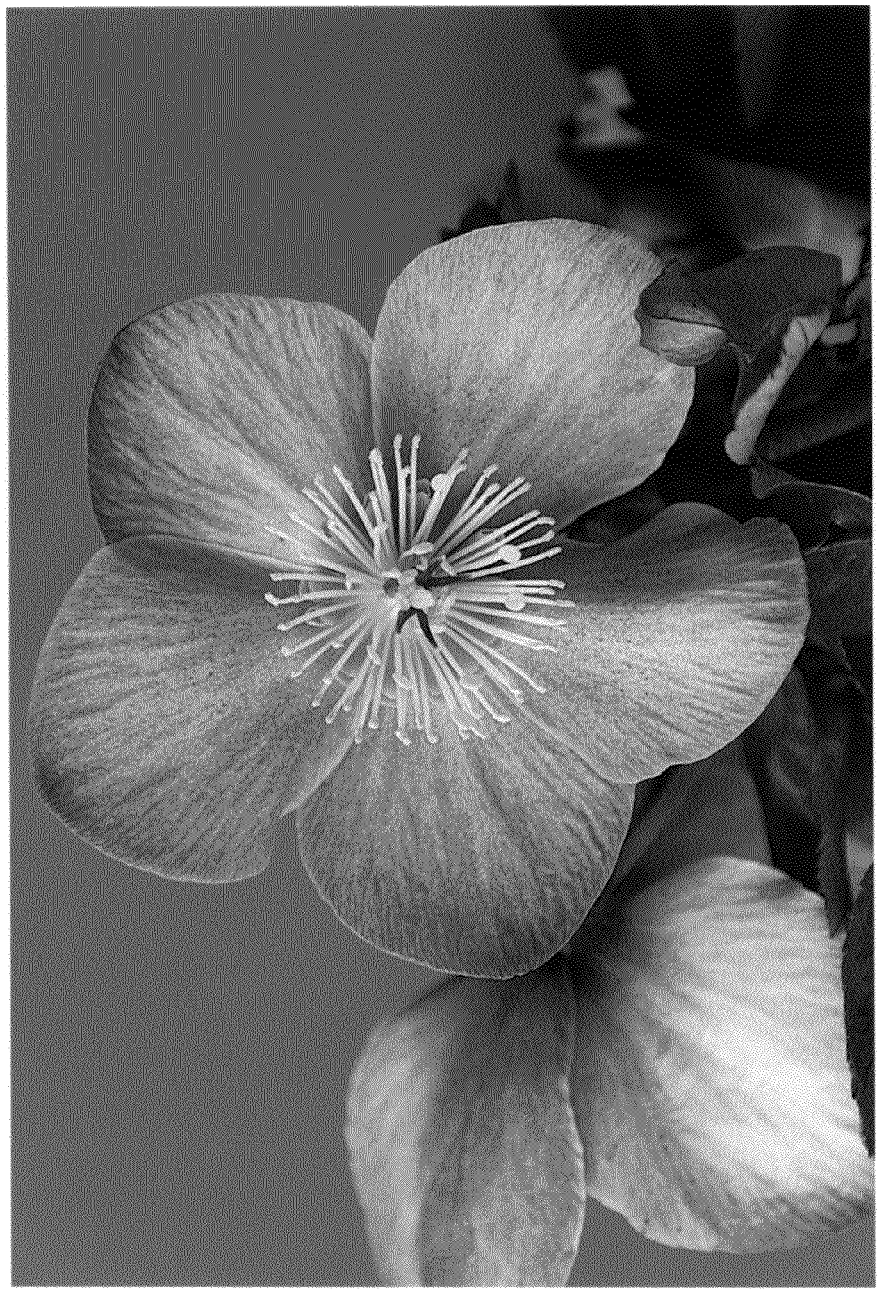

* * * * *